US008840556B2

(12) United States Patent
Lin et al.

(10) Patent No.: US 8,840,556 B2
(45) Date of Patent: Sep. 23, 2014

(54) SKULL ENDOSSEOUS MODULE FOR ULTRASOUND PENETRATION

(71) Applicant: National Cheng Kung University, Tainan (TW)

(72) Inventors: Chou-ching Lin, Tainan (TW); Chia-chu Chiang, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 13/710,702

(22) Filed: Dec. 11, 2012

(65) Prior Publication Data

US 2013/0345599 A1 Dec. 26, 2013

(30) Foreign Application Priority Data

Jun. 22, 2012 (TW) .............................. 101122426 A

(51) Int. Cl.
*A61B 8/00* (2006.01)
*A61B 19/00* (2006.01)
*A61N 7/00* (2006.01)
*A61B 8/08* (2006.01)

(52) U.S. Cl.
CPC ................ *A61N 7/00* (2013.01); *A61B 19/201* (2013.01); *A61B 8/0808* (2013.01)
USPC ............. 600/441; 600/437; 623/17.19; 601/2

(58) Field of Classification Search
USPC ...................... 600/437, 441; 601/2; 623/17.19
See application file for complete search history.

(56) References Cited

U.S. PATENT DOCUMENTS

2009/0248165 A1* 10/2009 Lin et al. ..................... 623/17.19
2011/0245951 A1* 10/2011 Gantes ............................ 700/98

* cited by examiner

*Primary Examiner* — Unsu Jung
*Assistant Examiner* — Joel Lamprecht
(74) *Attorney, Agent, or Firm* — Muncy, Geissler, Olds & Lowe, P.C.

(57) ABSTRACT

A skull endosseous module for ultrasound penetration is provided and includes a fixation sleeve permanently inserted and positioned in a drilled hole of a skull, a movable sleeve movably inserted in the fixation sleeve for providing a hollow ultrasound guiding channel; and an outer cover mounted on an outer opening of the fixation sleeve and covered by a scalp tissue. Thus, an ultrasound device outside the scalp tissue can generate ultrasounds to pass through the outer cover and the ultrasound guiding channel for affecting a target region of a brain tissue in the skull.

11 Claims, 6 Drawing Sheets

SKULL ENDOSSEOUS MODULE FOR ULTRASOUND PENETRATION

CROSS-REFERENCE TO RELATED APPLICATION

This application claims priority from and the benefit under 35 U.S.C. §119(a) of Taiwan Patent Application No. 101122426, filed on Jun. 22, 2012 in the TIPO (Taiwan Intellectual Property Office of the R.O.C), which is hereby incorporated by reference for all purposes as if fully set forth herein.

FIELD OF THE INVENTION

The present invention relates to a skull endosseous module for ultrasound penetration, and more particularly to a skull endosseous module for ultrasound penetration permanently inserted in a drilled hole of a skull and covered by a scalp.

BACKGROUND OF THE INVENTION

Recently, many researches have confirmed that focused ultrasound technology has therapeutic effect for biological tissues and can partially improve thrombosis thereof, so as to further be used for treating or preventing a stroke. However, most of conventional ultrasound systems for treating thrombosis are high frequency type, wherein the energy of high frequency encounters severe skull absorption and focal beam distortion to make the intracranial therapy becomes difficult, so that the ultrasonic waves can not be focused on a target region. Therefore, the actual effect of the ultrasonic waves is significantly reduced in application to thrombosis.

To solve the foregoing problems, two types of the conventional ultrasound devices in application are mainly divided into invasive type and non-invasive type. For the non-invasive ultrasound device, it generally can be used and directly improved in-vitro without cutting the scalp and drilling the skull. For example, one set of low frequency multiple-channel focused ultrasound phased array driving system is designed and comprises a multiple-channel driving module, a multiple-channel power detection module, and a hemispherical ultrasound phased array transducer, wherein each array unit of the hemispherical ultrasound phased array transducer can generate a focus point in a space of the brain of a wearer. Phase variation of each array unit can change the focus point of ultrasonic waves, so as to provide functions of electronic phase-shift focusing and real-time power monitoring. However, to allow the ultrasonic waves to penetrate through the skull, the conformation of the foregoing in-vitro ultrasound device becomes extremely complicated and further increases the costs of equipment and treatment. Furthermore, most of ultrasonic waves encounter severe skull absorption during ultrasounds penetrate through the skull, so that the actual therapeutic effect is still considerably limited.

On the other hand, for the invasive ultrasound device, it generally needs to cut the scalp and drill the skull for forming a hole and inserting a fixed channel apparatus, so that an outer cover is exposed out of the scalp. When needing to apply the ultrasonic waves for treating the intracranial brain of a patient, medical personnel can open the outer cover to insert the ultrasonic apparatus into the skull, so as to emit the ultrasonic waves for treating a target region and cause the signal of visible light transmitting into the skull easily. After finishing image detection, the outer cover is closed rapidly. However, the fixed channel apparatus connecting to the outside has an infective risk to the intracranial brain and affects the appearance of the scalp.

Moreover, another invasive ultrasound device is to insert an artificial skull apparatus after directly drilling the skull, wherein the apparatus is directly covered by the scalp and comprises a channel and a wireless remote controlled cover body. Medical personnel can open the cover body in vitro by wireless remote controlling for using an in-vitro ultrasound device to deliver the ultrasonic waves into the therapeutic region. After treating, the medical personnel then can close the cover body in vitro by wireless remote controlling, and the cover body provides a skull-like function. However, the problems of the device are that a battery and a circuit module must be built-in. Although the battery could be charged wirelessly, but when an energy storage function of the battery is lost or the circuit module is destroyed, the cover body can not be opened. Because the ultrasonic waves can not penetrate through the cover body, so that a surgery operation is needed for repairing or replacing components. As a result, it causes an inconvenience in long-term usage.

As a result, it is necessary to provide a skull endosseous module for ultrasound penetration to solve the problems existing in the conventional technologies, as described above.

SUMMARY OF THE INVENTION

A primary object of the present invention is to provide a skull endosseous module for ultrasound penetration, which comprises: a fixation sleeve permanently inserted and positioned in a drilled hole of a skull, a movable sleeve movably inserted in the fixation sleeve to provide a hollow ultrasound guiding channel therein, and an outer cover connected and covered on an outer opening of the fixation sleeve, wherein the outer cover is covered by a scalp tissue of the subject. Therefore, it only needs to operate a craniotomy once for inserting a skull endosseous module onto the skull of a subject, after that, it is unnecessary to do the craniotomy operation again, and thus an ultrasound device is directly disposed outside of the scalp tissue to generate ultrasounds to pass through the outer cover and the ultrasound guiding channel for affecting a brain tissue in the skull. As a result, it can relatively simplify the conformation of an implant and increase the convenience of long-lasting application.

A secondary object of the present invention is to provide a skull endosseous module for ultrasound penetration, which further comprises a tilting controller fixed between the fixation sleeve and the outer cover, wherein the tilting controller has a plurality of inclination controlling components which can selectively pull or push the movable sleeve to change a tilted angle of the ultrasound guiding channel of the movable sleeve in relation to the receiving space of the fixation sleeve, so as to guild ultrasound waves to be focused on the target region of a brain to relatively increase the accuracy of emitting the ultrasonic waves.

To achieve the above object, the present invention provides a skull endosseous module for ultrasound penetration, which comprises:

a fixation sleeve permanently inserted and positioned in a drilled hole of a skull of a subject, wherein the fixation sleeve has a hollow receiving space, and an inner circumference of the receiving space is formed with an inner flange;

a movable sleeve movably inserted in the receiving space of the fixation sleeve, wherein the movable sleeve is provided with a hollow ultrasound guiding channel therein, and an outer circumference of the movable sleeve is formed with an outer flange, the outer flange is movably disposed on the inner flange; and an outer cover connected and covered on an outer opening of the fixation sleeve, so as to close the receiving space, wherein the outer cover is covered by a scalp tissue of the subject.

In one embodiment of the present invention, an ultrasound device is disposed outside the scalp tissue, so as to generate ultrasounds to pass through the outer cover and the ultrasound guiding channel for affecting a brain tissue in the skull.

In one embodiment of the present invention, the ultrasound guiding channel of the movable sleeve has an outer opening and an inner opening, and the ultrasound guiding channel is tapered from the outer opening to the inner opening, so that the ultrasound wave passing through the ultrasound guiding channel is focused on the brain tissue.

In one embodiment of the present invention, the fixation sleeve is made of biocompatible metal or alloy, such as titanium or titanium alloy.

In one embodiment of the present invention, the movable sleeve is made of non-metal material with biocompatibility and ultrasound penetration property, such as silicone or thermoplastic elastomer.

In one embodiment of the present invention, the outer cover is made of plastic or rubber material with biocompatibility and ultrasound penetration property, such as polyethylene or other polymer resins.

In one embodiment of the present invention, the ultrasound guiding channel of the movable sleeve is parallel to the receiving space of the fixation sleeve (an angle between both axial directions of them is 0 degree).

In one embodiment of the present invention, the skull endosseous module for ultrasound penetration further comprises a tilting controller fixed between the outer opening and the outer cover of the fixation sleeve, wherein the titled controller has a plurality of inclination controlling components, one of the plurality of inclination controlling components is selected to pull or push the movable sleeve to change a tilted angle of the ultrasound guiding channel of the movable sleeve in relation to the receiving space of the fixation sleeve.

In one embodiment of the present invention, the inclination controller is made of biocompatible metal or alloy, such as titanium or titanium alloy, wherein the titanium alloy may be nickel-titanium shape-memory alloy.

In one embodiment of the present invention, the inclination controlling component is selected from a manual-operated type, thermal-driven type or pressure-driven type inclination controlling component.

In one embodiment of the present invention, the tilted angle is between 30 degree and 45 degree.

In one embodiment of the present invention, the tilting controller is a ring member and the inclination controlling components are symmetrically arranged on the ring member.

DETAILED DESCRIPTION OF THE PREFERRED EMBODIMENTS

The structure and the technical means adopted by the present invention to achieve the above and other objects can be best understood by referring to the following detailed description of the preferred embodiments and the accompanying drawings. Furthermore, directional terms described by the present invention, such as upper, lower, front, back, left, right, inner, outer, side, longitudinal/vertical, transverse/horizontal, and etc., are only directions by referring to the accompanying drawings, and thus the used directional terms are used to describe and understand the present invention, but the present invention is not limited thereto.

Figure 1:
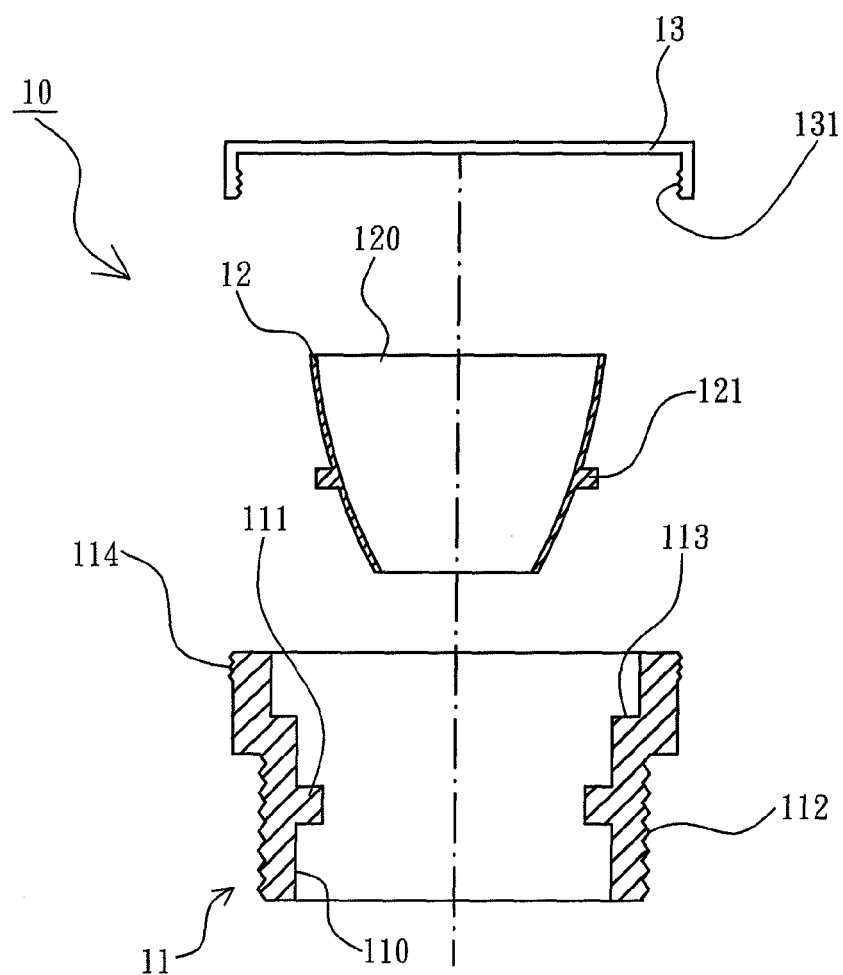
FIG. 1 is a cross-sectional view of a skull endosseous module for ultrasound penetration according to a first embodiment of the present invention.

Referring to FIG. 1, a skull endosseous module for ultrasound penetration according to a first embodiment of the present invention is illustrated. As shown, a skull endosseous module for ultrasound penetration 10 comprises: a fixation sleeve 11, a movable sleeve 12 and an outer cover 13. The present invention describes the detail structures, the assembly relationship and the operative principle of each forgoing element in the first embodiment more detailed according to FIGS. 1 to 3 hereinafter.

First, Referring to FIG. 1, in the first embodiment of the present invention, the fixation sleeve 11 is a hollow tubular element and made of biocompatible metal or alloy, such as titanium (Ti) or titanium alloy, but not limited thereto. The fixation sleeve 11 has a hollow receiving space 110, and an inner circumference of the receiving space 110 is formed with an inner flange 111. Moreover, two ends of the receiving space 110 of the fixation sleeve 11 have an upward outer opening and downward inner opening (unlabeled), respectively. And, the fixation sleeve 11 is formed with a large diameter portion with a relatively larger diameter, which is relatively closed to the outer opening, and a small diameter portion with a relatively smaller diameter, which is relatively closed to the inner opening, so as to form a stepped portion 113 at the junction between the large and small diameter portions and relatively close to the outer opening side. The outer circumference of the small diameter portion of the fixation sleeve 11 is formed with an outer thread 112, and if necessary, the outer circumference of the large diameter portion of the fixation sleeve 11 is also formed with another outer thread 114. The size of the fixation sleeve 11 is designed in relation to the skull size of the subject to which the fixation sleeve 11 is inserted, and the present invention is not limited thereto.

Referring to FIG. 1 again, in the first embodiment of the present invention, the movable sleeve 12 is another hollow tubular element and made of non-metal material with biocompatibility and ultrasound penetration property, such as silicone or thermoplastic elastomer, but not limited thereto. The movable sleeve 12 is movable inserted into the receiving space 110 of the fixation sleeve 11. The movable sleeve 12 has a hollow ultrasound guiding channel 120 therein, and the outer circumference of the movable sleeve 12 is formed with an outer flange 121. The outer diameter of the outer flange 121 is smaller than the inner diameter of the receiving space 110, and the outer circumference of the movable sleeve 12 disposed below the outer flange 121 has an outer diameter smaller than the inner diameter of the inner flange 111, so that the movable sleeve 12 is movably and rotatably disposed on the inner flange 111 by the outer flange 121. Moreover, the ultrasound guiding channel 120 of the movable 12 has an upward outer opening and downward inner opening (unlabeled), wherein the ultrasound guiding channel 120 is preferably tapered from the outer opening to the inner opening, so as to provide a function of focusing the ultrasonic waves.

Referring still to FIG. 1 again, in the first embodiment of the present invention, the outer cover 13 is made of plastic or rubber material with biocompatibility and ultrasound penetration property, such as polyethylene resin or other polymer resins. In the present embodiment, the outer cover 13 must have sufficient hardness as the same as the skull to provide protection for the brain. The inner diameter of the outer cover 13 is equal to the outer diameter of the outer circumference of the fixation sleeve 11 close to the outer opening side. In the meantime, the inner circumference of the outer cover 13 has an inner thread 131, wherein the inner thread 131 can connect to the outer thread 114, so that the outer cover 13 can connect to and cover on the outer opening of the fixation sleeve 11, in order to close the receiving space 110.

Figure 2:
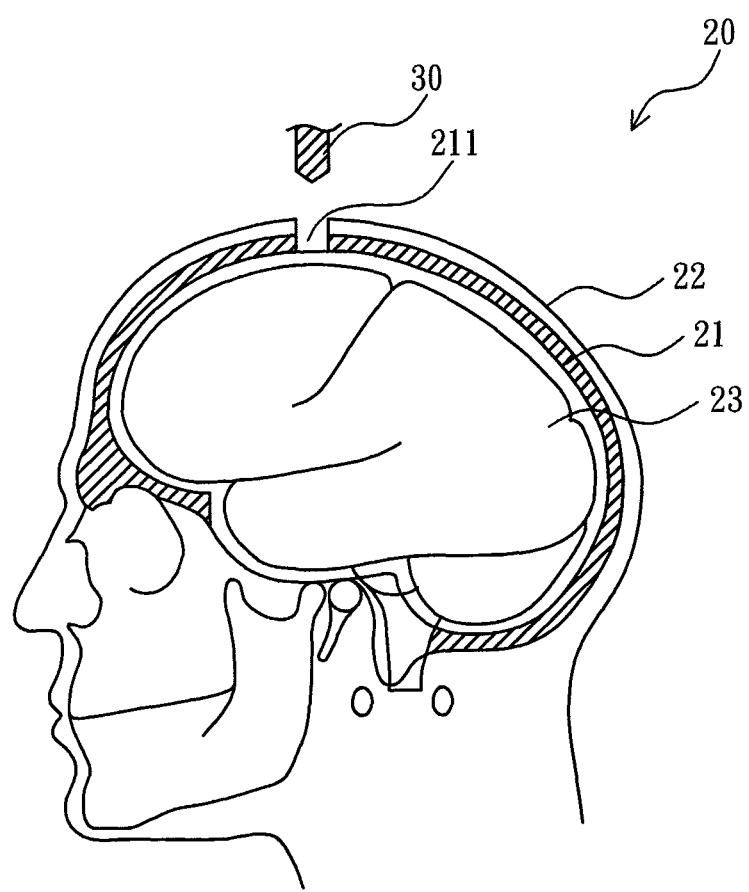
FIG. 2 is a schematic view of a craniotomy in the skull according to the first embodiment of the present invention.

Referring to FIG. 2, when the ultrasound penetration module 10 is installed on the skull 21 of a subject 20 (such as human beings), a scalpel firstly cuts scalp tissues 22 to expose the skull 21. Next, a drilling apparatus 30 is used to carry out a craniotomy for the skull 21 to form a drilled hole 211, wherein the inner diameter of the drilled hole 211 is equal to or slightly smaller than the outer diameter of the small diameter portion of the fixation sleeve 11, so that the drilled hole 211 exposes a brain tissue and surface membrane layers (such as dura mater, arachnoid and pia mater) of the skull 21.

Figure 3:
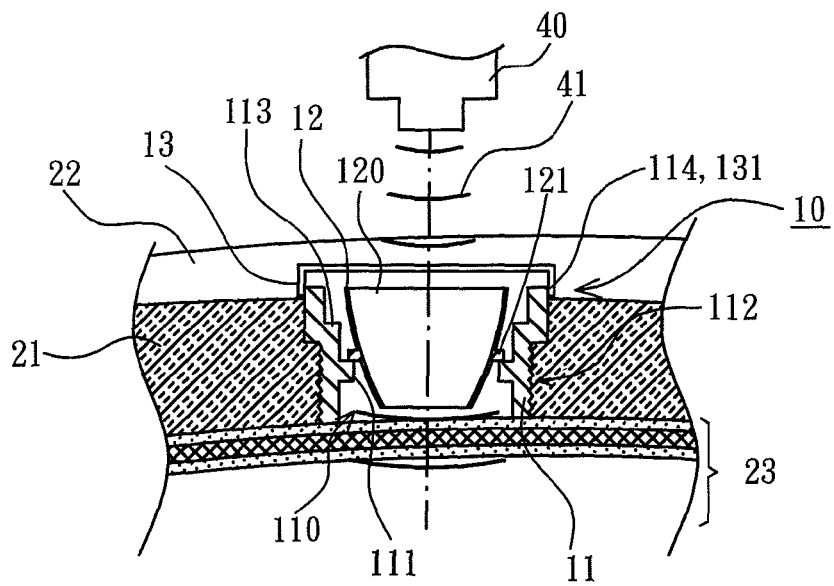
FIG. 3 is an operational view of the skull endosseous module for ultrasound penetration for ultrasound treatment according to the first embodiment of the present invention.

Therefore, Referring to FIG. 3, the fixation sleeve 11 is further permanently inserted into the drilled hole 211 of the skull 21 by using a tool. In the meantime, the outer thread 112 on the outer circumference of the small diameter portion of the fixation sleeve 11 is tightly screw-connected to the inner surface of the drilled hole 211 and the stepped portion 113 of the fixation sleeve 11 is tightly connected to the surface of the skull 21 or slightly sunk into the skull 21. After that, the movable sleeve 12 can be movably inserted into the receiving space 110 of the fixation sleeve 11, wherein the outer flange 121 is movably and rotatably disposed on the inner flange 111 and supported to the inner flange 111. In the meantime, an axial direction of the ultrasound guiding channel 120 of the movable sleeve 12 is parallel to an axial direction of the receiving space 110 of the fixation sleeve 11, i.e. an angle therebetween is 0 degree.

Next, the inner thread 131 of the outer cover 13 is screw-connected to the outer thread 114 (or by using other connection method, such as tight connection), so that the outer cover 13 can connect to and cover on the outer opening of the fixation sleeve 11 for closing the receiving space 110. Finally, the scalp tissues 22 are sutured by using surgery, so that the ultrasound penetration module 10 is totally covered and protected by the scalp tissues 22 finally.

Referring to FIG. 3 again, when the brain tissue 23 of the subject 20 is treated by applying the ultrasonic waves, the present invention further uses an ultrasound device 40. The ultrasound device 40 is disposed directly over the ultrasound penetration module 10, so as to deliver the ultrasonic waves outside the scalp tissues 22. The ultrasonic waves 41 can penetrate through the scalp tissues 22, the outer cover 13 and the ultrasound guiding channel 120 of the movable sleeve 12 in turn, so that the ultrasonic waves 41 can affect a target region of the brain tissue 23 under the ultrasound penetration module 10. Hereby, the present invention only needs to operate craniotomy once to the subject 20 for permanently inserting the ultrasound penetration module 10 without any further surgery in the future, so that the ultrasound device 40 can easily deliver the ultrasonic waves from outside to the target region of the brain tissue 23.

Figure 4:
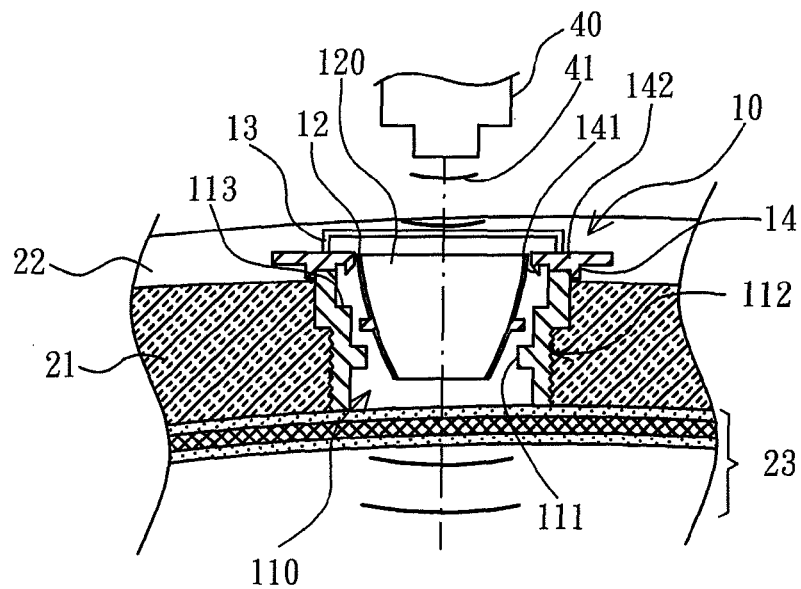
FIG. 4 is an assembled cross-sectional view of the skull endosseous module for ultrasound penetration according to a second embodiment of the present invention.
Figure 5:
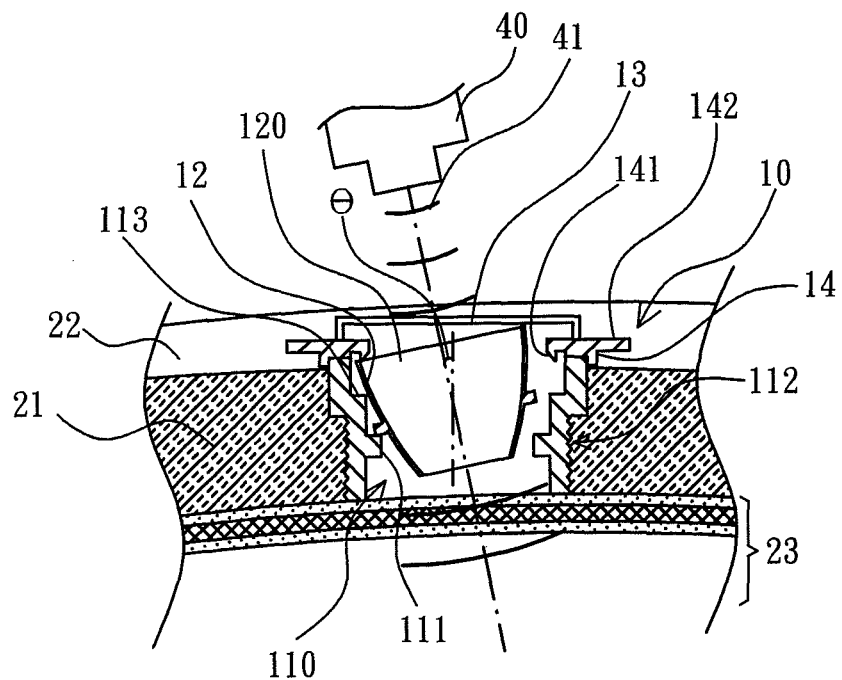
FIG. 5 is an operational view of the skull endosseous module for ultrasound penetration for ultrasound treatment according to the second embodiment of the present invention.
Figure 5A:
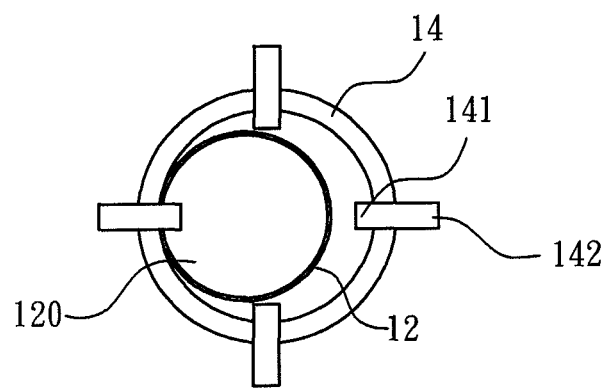
FIG. 5A is a top view of a titled controller and movable sleeve according to the FIG. 5 of the present invention.

Referring to FIGS. 4, 5 and 5A, a skull endosseous module for ultrasound penetration according to a second embodiment of the present invention is similar to the first embodiment of the present invention, so that the second embodiment uses similar terms or numerals of the first embodiment, but the different feature of the second embodiment is that the ultrasound penetration module 10 of the second embodiment further has a tilting controller 14, which is fixed between the outer opening of the fixation sleeve 11 and the outer cover 13, wherein the tilting controller 14 is made of biocompatible metal or alloy, such as titanium (Ti) or titanium alloy, and the titanium alloy is preferably selected from nickel-titanium shaped-memory alloy, but not limited thereto. In the present invention, the tilting controller 14 is a ring member, wherein a plurality of manual-operated type inclination controlling components are symmetrically arranged on the ring member, for example, four inclination controlling components are equidistantly and symmetrically arranged on the ring member, but the number thereof is not limited thereto, for example, the number can be 2, 3, 5, 6 or more. The fixation sleeve 11, the movable sleeve 12, the tilting controller 14 and the outer cover 13 of the embodiment are permanently mounted onto the skull 21, and are covered and protected by the scalp tissues 22.

Moreover, each of the inclination controlling components comprises a hook portion 141 and a press plate 142, wherein the hook portion 141 is radially protruded and extended inward from the ring member, and the press plate 142 is radially protruded and extended outward from the ring member. Moreover, the outer cover 13 is connected to the tilting controller 14 by thread, insertion or other suitable means. The outer cover 13 must be made of soft plastic or rubber material with biocompatibility and ultrasound penetration property to indirectly adjust the movable sleeve 12 through the outer cover 13 by fingers.

Referring to FIGS. 5 and 5A, in the embodiment, when the movable sleeve 12 is tilted by using one of the inclination controlling components, the movable sleeve 12 is indirectly adjusted through the outer cover 13 by fingers of an operator at first, so that the movable sleeve 12 is tilted to one particular inclination controlling component until a lip edge of the outer opening of the movable sleeve 12 is hooked (pulled) by the hook portion 141 of the inclination controlling component. A predefined tilted angle θ of the movable sleeve 12 is maintained by the hook portion 141, wherein the tilted angle θ means an angle of an axial direction of the ultrasound guiding channel 120 of the movable sleeve 12 in relation to an axial direction of the receiving space 110 of the fixation sleeve 11. The tilted angle θ is predetermined to each angle between 30 degree and 45 degree, such as 30°, 36°, 40° or 45° and so on, but not limited thereto.

Hereby, when the brain tissue 23 of the subject 20 is treated by the ultrasounds, an ultrasound device 40 is used. The ultrasound device 40 is disposed over the ultrasound penetration module 10 based on the same tilted angle θ (such as 30°), so as to deliver the ultrasonic waves 41 outside the scalp tissues 22 in a tilted manner. The ultrasonic waves 41 are transmitted into the scalp tissues 22, the outer cover 13 and the ultrasound guiding channel 120 of the movable sleeve 12 (having the tilted angle θ) in turn, so that the ultrasonic waves can affect a target region of the adjacent brain tissue 23 adjacent to the brain tissue 23 under the ultrasound penetration module 10.

Then, after finishing the treatment, the press plate 142 of the inclination controlling components is pressed downward by fingers of the operator, so that the hook 141 is correspondingly lifted upward, so as to release the snap relationship of the hook 141 and the movable sleeve 12, so that the movable sleeve 12 is returned back to original position, i.e. returned to a status that the ultrasound guiding channel 120 of the movable sleeve 12 is parallel to the receiving space 110 of the fixation sleeve 11 (an angle therebetween is 0 degree) before the inclination controlling component pulls the movable sleeve 12. If wanting to change the tilted direction again, the movable sleeve 12 is adjusted again indirectly through the outer cover 13 according to the forgoing method, so that the hook portion 141 of another inclination controlling component hooks the lip edge of the outer opening of the movable sleeve 12. The tilting controller 14 can cause the ultrasound guiding channel 120 to be tilted, so as to change the direction and angle of the ultrasonic waves 41 to irradiate the target region in the brain 23. Thus, the accuracy of emitting the ultrasonic waves can be relatively increased.

Figure 6:
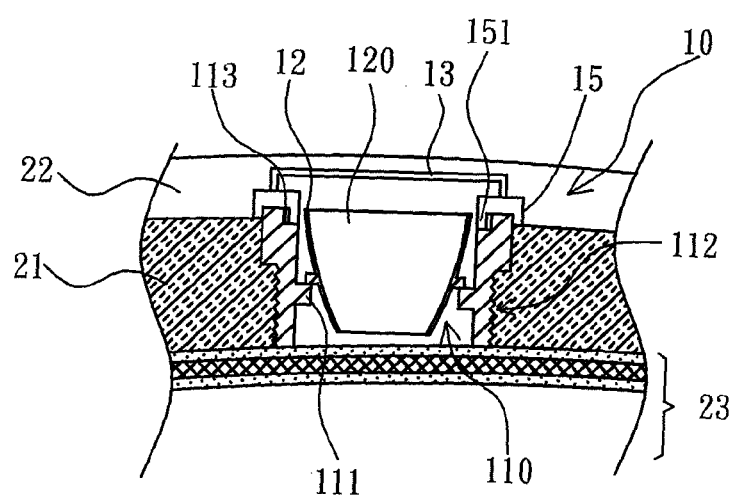
FIG. 6 is an assembled cross-sectional view of the skull endosseous module for ultrasound penetration according to a third embodiment of the present invention.
Figure 7:
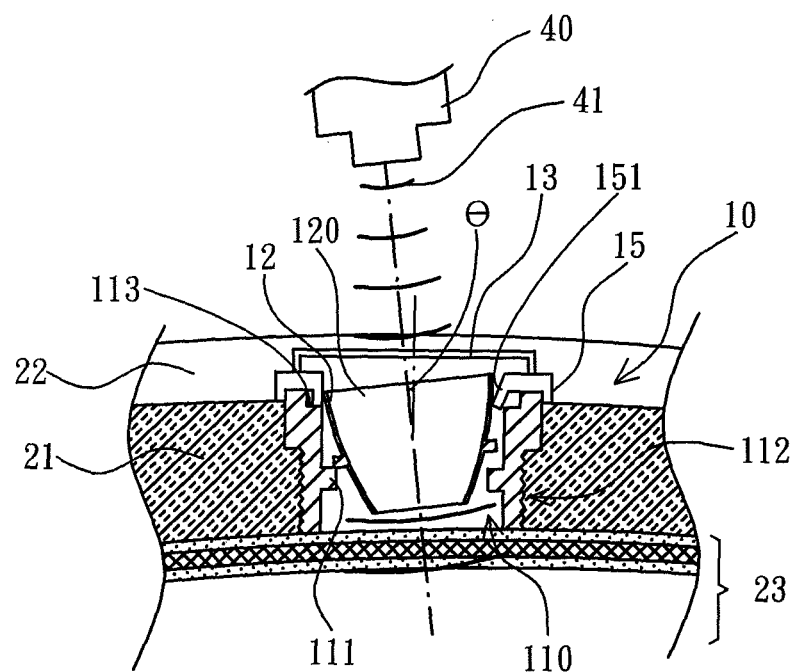
FIG. 7 is an operational view of the skull endosseous module for ultrasound penetration for ultrasound treatment according to the third embodiment of the present invention.
Figure 7A:
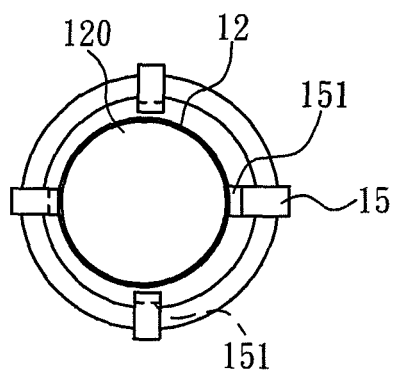
FIG. 7A is a top view of a titled controller and movable sleeve according to the FIG. 7 of the present invention.

Referring to FIGS. 6, 7 and 7A, a skull endosseous module for ultrasound penetration according to a third embodiment of the present invention is similar to the second embodiment of the present invention, so that the third embodiment uses similar terms or numerals of the second embodiment, but the difference feature of the third embodiment is that the tilting controller 15 of the ultrasound penetration module 10 of the third embodiment are a plurality of thermal-driven type or pressure-driven type inclination controlling components symmetrically arranged on the ring member, and each of the inclination controlling components comprises an actuator 151, wherein the actuator 151 is radially protruded and extended inward from the ring member. For the thermal-driven type, the inclination controlling components of the tilting controller 15 are made of biocompatible multi-layer composite metal or semiconductor layers. Coefficient of thermal expansion (CTE) of each of metal or semiconductor layers is different. The fixation sleeve 11, the movable sleeve 12, the tilting controller 15 and the outer cover 13 of the embodiment are permanently fixed on the skull 21, and thus are covered and protected by the scalp tissues 22.

Referring to FIGS. 7 and 7A, in the present embodiment, when one of the inclination controlling components is used to tilt the movable sleeve 12, an operator uses a heating apparatus (such as infrared heater) to the scalp tissues 22 over one particular inclination controlling component at first, and thus can indirectly heat the particular inclination controlling component outside the scalp tissues 22. Because of the multi-layer composite metal or semiconductor layers of the inclination controlling components is different, so as to generate different expansion degree during heating. Thus, the actuator 151 of the inclination controlling components is protruded and extended inward after heating to push the outer circumference of the movable sleeve 12, so that the movable sleeve 12 is tilted to the opposite side. The continuously heated actuator 151 can maintain the movable sleeve 12 with a predefined tilted angle θ (one angle between 30 degree and 45 degree).

Hereby, the ultrasound device 40 is used to emit the ultrasonic waves 41 from outside of the scalp tissues 22, and the ultrasonic waves 41 penetrate through the scalp tissues 22, the outer cover 13 and the ultrasound guiding channels 120 of the movable sleeve 12 (having a tilted angle θ), so that the ultrasonic waves 41 can affect a target region of the adjacent brain tissue 23 adjacent to the brain tissue 23 under the ultrasound penetration module 10.

Subsequently, after finishing the treatment, the operator can turn off or remove the heater, the actuator 151 is returned to original status after cooling, so that it is not necessary to push the movable sleeve 12 to return the movable sleeve 12 back to the original position, that is, return to a status that the ultrasound guiding channel 120 of the movable sleeve 12 is parallel to the receiving space 110 of the fixation sleeve 11 (an angle therebetween is 0 degree). If wanting to change the tilted direction, one particular inclination controlling component can be heated again as the forgoing method. Because the tilting controller 15 can tilt the ultrasound guiding channel 120 to change the emitting direction and angle of the ultrasonic waves 41 to irradiate the target region of the brain 23, the accuracy of emitting the ultrasonic waves 41 can be relatively increased.

Similarly, in another variation of the embodiment, the inclination controlling components of the forgoing tilting controller 15 also can be pressure-driven type, wherein the actuator 151 of each inclination controlling components is made of biocompatible metal or semiconductor layers. The metal or semiconductor layers are produced by micro-electromechanical systems (MEMS) or similar technologies to form an air chamber inside (not shown). In operation, the operator uses a simple mechanical press method (or uses an in-vitro wireless induction device to generate electric power for driving a related press apparatus of the inclination controlling components to press the air chamber) outside the scalp tissues 22 over one particular inclination controlling component, in order to indirectly control the actuator 151 of the particular inclination controlling component. Therefore, after controlling, the actuator 151 of the inclination controlling components is protruded and extended inward to push the outer circumference of the movable sleeve 12, so that the movable sleeve 12 can be maintain at the predefined tilted angle θ.

As described above, according to FIGS. 1 to 7A of the present invention, the fixation sleeve 11 is permanently inserted into the drilled hole 211 of the skull 21, wherein the movable sleeve 12 is movably inserted in the receiving space of the fixation sleeve 11 to provide with a hollow ultrasound guiding channel 120, an outer cover 13 is connected to the outer opening of the fixation sleeve 11, and the outer cover 13 is covered by the scalp tissues 22 of the subject 20. Therefore, the subject 20 only needs to operate craniotomy once for permanently inserting the module without any further surgery in the future, so that the ultrasound device 40 is used outside the scalp tissues 22 to transmit the ultrasonic waves 41 through the outer cover 13 and the ultrasound guiding channel 120 for affecting the brain 23 within the skull 21. Thus, the implant structure is relatively simplified and the convenience for long-term application can be increased.

Furthermore, the present invention further comprises the tilting controllers 14,15, which is fixed within the fixation sleeve 11 and the outer cover 13. The tilting controllers 14,15 have a plurality of the inclination controlling components to selectively pull or push the movable sleeve 12, in order to change a tilted angle θ of the ultrasound guiding channel 120 of the movable sleeve 12 in relation to the receiving space 110 of the fixation sleeve 11 for guiding the ultrasonic waves 41 to irradiate the target region of the brain, so as to relatively increase the accuracy of emitting the ultrasonic waves.

The present invention has been described with a preferred embodiment thereof and it is understood that many changes and modifications to the described embodiment can be carried out without departing from the scope and the spirit of the invention that is intended to be limited only by the appended claims.

What is claimed is:

1. A skull endosseous module for ultrasound penetration, comprising:
    a fixation sleeve configured to be permanently inserted and positioned in a drilled hole of a skull of a subject, wherein the fixation sleeve has a hollow receiving space, and an inner circumference of the receiving space is formed with an inner flange;
    a movable sleeve movably inserted in the receiving space of the fixation sleeve, wherein the movable sleeve is provided with a hollow ultrasound guiding channel therein, and an outer circumference of the movable sleeve is formed with an outer flange, the outer flange is movably disposed on the inner flange;
    an outer cover connected and covered on an outer opening of the fixation sleeve, so as to close the receiving space, wherein the outer cover is configured to be covered by a scalp tissue of the subject; and
    a tilting controller fixed between the outer opening and the outer cover of the fixation sleeve, wherein the tilting controller has a plurality of inclination controlling components, one of the plurality of inclination controlling components is selected to pull or push the movable sleeve to change a tilted angle of the ultrasound guiding channel of the movable sleeve in relation to the receiving space of the fixation sleeve.

2. The skull endosseous module for ultrasound penetration according to claim 1, wherein an ultrasound device is disposed outside the scalp tissue, so as to generate ultrasounds to pass through the outer cover and the ultrasound guiding channel for affecting a brain tissue in the skull.

3. The skull endosseous module for ultrasound penetration according to claim 2, wherein the ultrasound guiding channel of the movable sleeve has an outer opening and an inner opening, and the ultrasound guiding channel is tapered from the outer opening to the inner opening, so that the ultrasound wave passing through the ultrasound guiding channel is focused on the brain tissue.

4. The skull endosseous module for ultrasound penetration according to claim 1, wherein the fixation sleeve is made of biocompatible metal or alloy.

5. The skull endosseous module for ultrasound penetration according to claim 1, wherein the movable sleeve is made of non-metal material with biocompatibility and ultrasound penetration property.

6. The skull endosseous module for ultrasound penetration according to claim 1, wherein the outer cover is made of plastic or rubber material with biocompatibility and ultrasound penetration property.

7. The skull endosseous module for ultrasound penetration according to claim 1, wherein the ultrasound guiding channel of the movable sleeve is parallel to the receiving space of the fixation sleeve.

8. The skull endosseous module for ultrasound penetration according to claim 1, wherein the inclination controller is made of biocompatible metal or alloy.

9. The skull endosseous module for ultrasound penetration according to claim 1, wherein the inclination controlling component is selected from a manual-operated type, thermal-driven type or pressure-driven type inclination controlling component.

10. The skull endosseous module for ultrasound penetration according to claim 1, wherein the tilted angle is between 30 degree and 45 degree.

11. The skull endosseous module for ultrasound penetration according to claim 1, wherein the tilting controller is a ring member and the inclination controlling components are symmetrically arranged on the ring member.

* * * * *